United States Patent [19]

Kustes et al.

[11] Patent Number: 4,540,681

[45] Date of Patent: Sep. 10, 1985

[54] CATALYST FOR THE METHANATION OF CARBON MONOXIDE IN SOUR GAS

[75] Inventors: William A. Kustes; Arthur L. Hausberger, both of Louisville, Ky.

[73] Assignee: United Catalysts, Inc., Louisville, Ky.

[21] Appl. No.: 382,984

[22] Filed: May 28, 1982

Related U.S. Application Data

[63] Continuation of Ser. No. 177,165, Aug. 18, 1980, abandoned.

[51] Int. Cl.$^3$ .................. B01J 21/14; B01J 23/76; B01J 21/00
[52] U.S. Cl. ................. 502/234; 502/252; 502/306; 502/314; 518/702; 518/714; 48/197 FM
[58] Field of Search ............ 252/457, 458, 465, 468, 252/452; 502/234, 252, 306, 314, 315

[56] References Cited

U.S. PATENT DOCUMENTS

| | | | |
|---|---|---|---|
| 2,342,249 | 2/1944 | Burk | 252/452 |
| 2,500,197 | 3/1950 | Michael et al. | 252/452 X |
| 2,697,066 | 12/1954 | Sieg | 252/452 X |
| 2,969,348 | 1/1961 | Fawcett | 252/452 X |
| 3,904,386 | 9/1975 | Graboski et al. | 518/714 X |
| 4,005,996 | 2/1977 | Hausberger et al. | 518/703 X |
| 4,151,191 | 4/1979 | Happel et al. | 518/714 |

OTHER PUBLICATIONS

Catalysis, vol. IV, Paul H. Emmett, Reinhold Publishing Corp., N.Y., 1956, pp. 494–507.

*Primary Examiner*—Carl F. Dees
*Attorney, Agent, or Firm*—William R. Price

[57] ABSTRACT

The invention involves the synergistic effect of the specific catalytic constituents on a specific series of carriers for the methanation of carbon monoxide in the presence of sulfur at relatively high temperatures and at low steam to gas ratios in the range of 0.2:1 or less. This effect was obtained with catalysts comprising the mixed sulfides and oxides of nickel and chromium supported on carriers comprising magnesium aluminate and magnesium silicate. Conversion of carbon monoxide to methane was in the range of from 40 to 80%. Tests of this combination of metal oxides and sulfides on other carriers and tests of other metal oxides and sulfides on the same carrier produced a much lower level of conversion.

8 Claims, 1 Drawing Figure

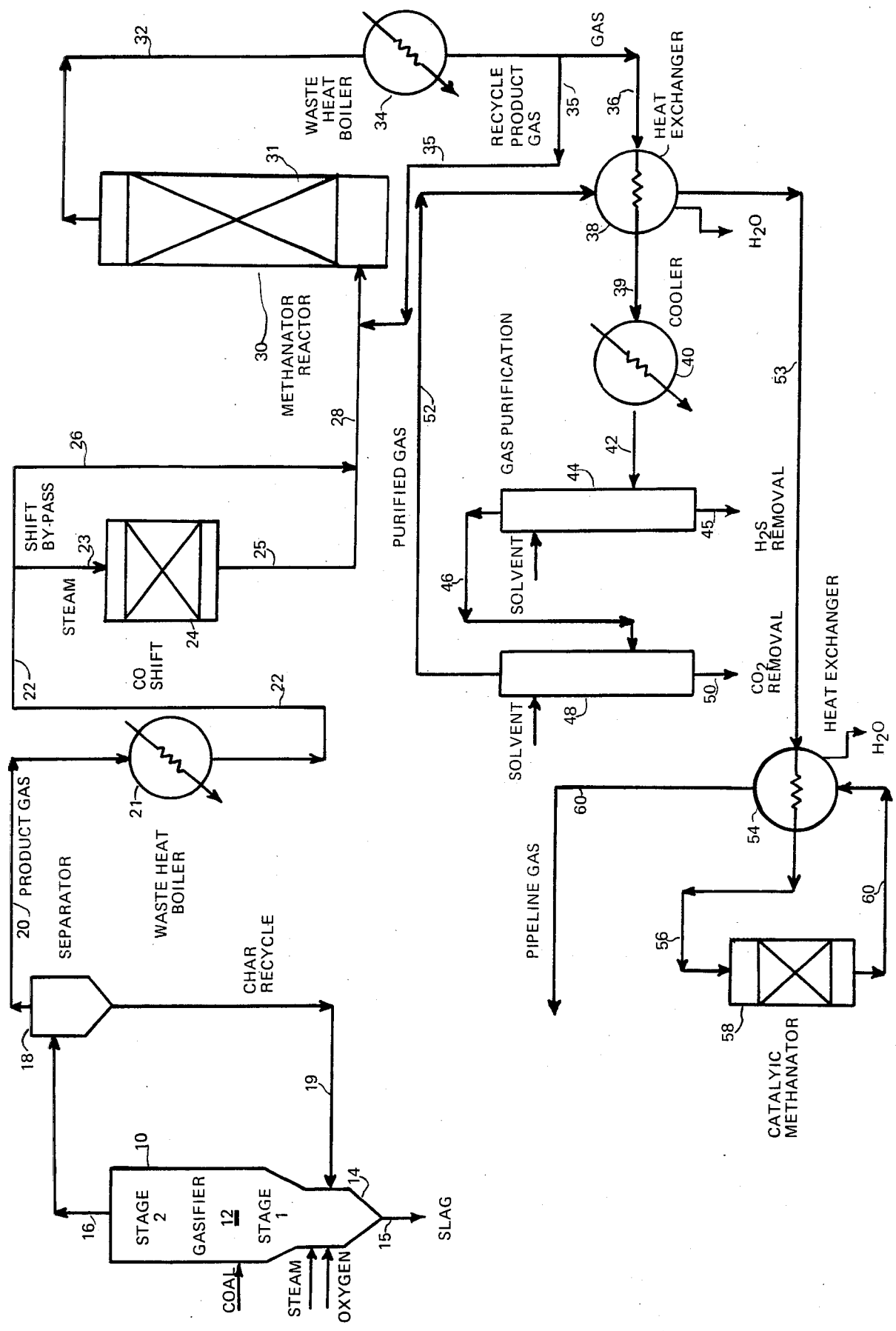

CATALYST FOR THE METHANATION OF CARBON MONOXIDE IN SOUR GAS

This application is based on data contained in a report by Arthur L. Hausberger and William A. Kustes, #FE-2039-9 UC902, entitled "Sulfur-resistant methanation catalyst", which was prepared for the United States Department of Energy, under contract number EX-76-6-01-20232.

This is a continuation of application Ser. No. 177,165 filed Aug. 18, 1980 now abandoned.

BACKGROUND OF THE INVENTION

The synthesis of methane by the hydrogenation of carbon monoxide has been known since first reported and described by Sabatier and Senderens in 1902. Further, production of gaseous fuel by the gasification of coal has been known and practiced for many years. As practiced in the early years in the United States and later throughout Europe a low BTU gas of about 500 BTU per cubic foot was produced. In the United States, however, the coal gas fuels have been largely superseded by natural gas. Thus, the U.S. economy is based on a high BTU fuel. Therefore, any fuel produced from coal or any other carbonaceous material must be interchangeable with natural gas so that the flame characteristics and other characteristics of the synthetic fuel will match that of natural gas. Furthermore, coal contains about five weight percent hydrogen and 75% carbon whereas natural gas contains about 25% weight percent hydrogen. It therefore is necessary to provide an extra source of hydrogen above that normally contained in coal gas, if a synthesis gas of the proper concentration is to be achieved. Normally this is achieved by the conversion of carbon monoxide with steam to produce additional hydrogen and $CO_2$ so that the proper stoichiometric ratio of hydrogen to CO is maintained in the initial gas mixture. The major problem, however, has been in the fact that the methanation catalysts have been notoriously sensitive to sulfur. This then required that all of the sulfur compounds be removed from the crude gas, prior to the methanation reaction over the sulfur sensitive nickel catalyst.

DESCRIPTION OF THE PRIOR ART

This was the approach utilized by Hausberger and Hammons in U.S. Pat. No. 4,005,996 in which the gasification products of coal were catalytically treated over a sulfur sensitive nickel catalyst to produce methane of pipeline quality. In this case, however, the sulfur in the crude gas emanating from the gasifier, was treated to remove all of the sulfur bearing constituents prior to being subjected to the methanation catalyst. Graboski, et al, in U.S. Pat. No. 3,904,386 treat the sulfur bearing gases from the gasifier in a shift and methanation reactor, whereby the hydrogen produced in the shift reaction is utilized in the methanation reaction. According to the inventors, the two reactions simultaneously taking place in the combined reactor system yield a methane rich product gas comprising above 40% by volume methane. In order to accomplish this however, it is necessary to add steam to the gases entering the shift and methanation reactor to produce a gas mixture having a steam/gas ratio of about 0.5. A wide range of catalysts are proposed by Graboski et al for this reaction including the single metal oxides, sulfides, or carbonates, or combinations of these from the group consisting of groups IB, VIB, or VIII plus alkali promoters from groups IA, IIA or the period 7 rare earths. Additionally, the catalyst may include chromium oxide, molybdenum oxide, or sulfide and iron oxide; mixtures of nickel oxide with oxides of chromium, molybdenum or tungsten or mixtures of cobalt oxide with oxides of chromium, molybdenum or tungsten. The support materials for the catalyst include silicate, magnesia-aluminum silicates, silica gel, magnesium silicate or mixed silicates such as magnesium aluminum silicate or molecular sieves. Further, the use of alkali metal promoters to retard carbon deposition was suggested.

More recently in U.S. Pat. No. 4,151,191 Happel and Hnatow of the American Gas Association have proposed the use of lanthanum series promoted cobalt, molybdenum oxide, molybdenum, aluminum oxides as catalysts for methanation in a sour gas. The time on stream for each of these catalysts was not recorded, but the percent conversion of carbon monoixde to methane ranged in the area of from 2.97 to 20%.

In another patent, U.S. Pat. No. 4,132,672, Henry Wise and Bernard Wood of the American Gas Association proposed the use of an iridium promoted nickel catalyst. These catalysts had a high initial conversion rate for CO to $CH_4$. This conversion rate declined some 50% in about 50 minutes.

SUMMARY OF THE INVENTION

According to this invention, it is possible to produce gas of pipeline quality from the gasification products of coal or other carbonaceous materials containing sulfur compounds. This is accomplished by subjecting a portion of the crude gasification product to the water gas shift reaction so as to raise the carbon monoxide to hydrogen ratio to at least 3:1 in entering the methanation reactor. Furthermore, according to this invention, the gases can be utilized with a steam to gas ratio of as low as 0.00:1 to about 0.2:1. Furthermore, relatively high temperatures can be utilized so that the shift reaction is essentially eliminated. According to this invention, then it is possible through the judicious choice of a catalyst composition, and a judicious choice of process conditions to selectively hydrogenate carbon monoxide to methane without deleterious deposition of carbon and without essentially any conversion of carbon monoxide to carbon dioxide.

BRIEF DESCRIPTION OF THE DRAWING

The drawing is a diagrammatic illustration of the apparatus used in the gasification of coal and in the hydrogenation of the carbon oxides derived therefrom to produce methane.

DESCRIPTION OF THE PREFERRED EMBODIMENT

In the synthesis of methane from carbon oxide, there are five chemical reactions which may take place simultaneously. These reactions are as follows:

1. $CO + 3H_2 \approx CH_4 + H_2O - 94{,}240$ BTU/lb. mol.
2. $CO_2 + 4H_2 \approx CH_4 + 2H_2O - 77.700$ BTU/lb. mol.
3. $CO + H_2O \approx CO_2 + H_2 - 16{,}500$ BTU/lb. mol.
4. $2CO \approx C + CO_2 - 37{,}277$ BTU/lb. mol. (BOUDOUARD REACTION)
5. $CH_4 \approx C + 2H_2 + 36.222$ BTU/lb. mol.

As will be noted, the first two reactions are highly exothermic reactions of hydrogen with carbon oxides to form methane. The third reaction is the water gas shift reaction. The final two reactions are the two principal reactions by which carbon can be formed in this system. Carbon is a highly undesirable, but a potential product in the methanation reaction. The exothermic nature of the reactions is a feature of major significance. Since the carbon monoxide concentration is high, it is necessary to provide a system which will prevent temperature runaway. Conventionally, high concentrations of steam and $CO_2$ have been utilized to act as diluents and therefore reduce the amount of carbon monoxide available for reaction, to act as heat sinks and to prevent the undesirable Boudouard reaction. Unfortunately, additional steam tends to promote the undesirable shift reaction with the production of additional $CO_2$. Since the primary object of the process is to produce methane, rather than $CO_2$, the steam to gas ratio is maintained at a minimum.

Throughout the specification coal is utilized as the raw material for the gasification process. It should be understood, however, that the term coal is intended to designate a carbonaceous material which could include all types of coal, lignite, or the like, and further that the gasification process is not limited to the gasification of coal and can also be used with oil, shale, heavy oil residues, tars, etc. Further, a two stage gasification system is indicated in the drawings. It should be understood, however, that other methods of gasification could be utilized such as: a Winkler gasification unit, a Saarberg/Otto unit, a Koppers-Totzek apparatus, A F.W.-Stoic gasifier, a Shell Koppers unit, a Lurgi-SNG unit, or any other system suitable for the production of synthesis gas from coal or other carbonaceous materials.

The term gasification means the heating of coal in the presence of reacting agents whereby all or part of the volatile portion of the coal is liberated and the carbon in the residual char is reacted with those agents or with other reactants present in the gasification process.

The term synthesis gas means a carbon oxide, hydrogen and methane containing gas such as the gas produced in the second stage of the two stage gasification process described herein.

The term product gas means a methane rich gas produced by the hydrogenation of carbon monoxide.

Referring now to the drawing, preheated coal is injected into the upper portion 10 of a two stage gasification vessel 12 as a reactant in the second stage of the gasification. The process is not limited to the use of a two stage gasification process for the production of a synthesis gas containing hydrogen, hydrogen sulfide, methane and the oxides of carbon. Any gasification in which carbonaceous materials are converted to a synthesis gas is acceptable for incorporation into the present invention. Therefore, reference in the present invention to a two stage gasification process for the production of synthesis gas is made for the purposes of illustration and example only.

Steam and oxygen are introduced into the lower portion of the vessel 14 and are reacted with the preheated char in the stage 1 of the gasification process to produce a synthesis gas containing hydrogen and carbon oxides. The synthesis gas flows upwardly through the gasifier vessel 12 for reaction in the upper portion 10 as stage 2 of the gasification process. The coal introduced in the vessel's upper portion 10 is pulverized to a sufficient particle size to permit entrainment of the pulverized coal with the synthesis gas flowing upwardly from the stage 1 to the stage 2. The reaction in the stage 2 of the gasification is conducted at a temperature in excess of 1600° F. and at a pressure in excess of 30 atmospheres with sufficient residence time for the reactants in the stage 2 of vessel 12 maintained to assure reaction of the coal. The product of the reaction of the second stage between the preheated coal and the synthesis gas is a low sulfur char entrained in a synthesis gas containing methane hydrogen and carbon oxides. The sulfur content of the char is maintained at a minimum level by reacting the pulverized coal with the synthesis gas in the presence of hydrogen and steam at elevated temperatures and pressures.

The low sulfur char entrained in the synthesis gas is withdrawn from the upper portion of the vessel 12 and fed through line 16 into the cyclone separator 18. The partially gasified char separated in cyclone separator 18 is withdrawn therefrom and fed through line 19 into the lower portion 14 of the gasifier vessel 12 as a reactant for stage 1 of the gasification process. Steam and oxygen are introduced into the lower portion 14 and are reacted with the char in the stage 1 of the gasification process to produce gas containing hydrogen and carbon oxides as previously indicated. The synthesis gas reacts in the upper portion 10 with the preheated coal in stage 2 of the gasification process. The molten slag formed in the gasifier vessel 12 gravitates to the bottom of the vessel where the molten slag is cooled and withdrawn through conduit 15. The hot synthesis gas exits from the top of separater 18 through line 20 to a waste heat boiler 21 where the synthesis gas is reduced from 1700° F. to a temperature of about 650°. During the cooling process in the boiler 21, feed water may be sprayed into the synthesis gas sufficiently to raise the moisture content within the product gas to a steam to dry gas ratio to provide hydrogen for the methanation synthesis. The cooled synthesis gas is led via line 22 through line 23 to carbon monoxide shift converter 24 wherein a portion of the carbon monoxide in the gas is reacted to produce hydrogen which exits the shift reactor 24 via line 25. A portion of the crude synthesis gas, however, goes to by-pass line 26 and the gas from both lines 25 and 26 meet at line 28 to go into the methanator reactor 30 containing the methanation catalyst 31 of this invention. This gas has a hydrogen to carbon monoxide ratio of at least 3:1. In other words, sufficient hydrogen is available from the original gasification process and the subsequent water gas shift process to meet the stoichmetric requirement of the methanation reaction.

In order to prevent an undue temperature rise in the catalyst bed 31, a portion of the recycled product gas is added from line 35 into line 28 to lower the amount of carbon monoxide at inlet 28 and thus limit the exothermic heat in the catalyst bed 31.

This can be illustrated by following the flow of the gas from the methanator 30 through line 32 and through waste heat boiler 34 back through recycle line 35 into the inlet line 28. A portion of the product gas, however, is conducted through line 36 to heat exchanger 38 for further cooling and passes through line 39 to another cooler for additional cooling to a temperature suitable for the selective removal of the acid gases. The product gas from the cooler is conducted through line 42 to a hydrogen sulfide removal unit 44. The hydrogen sulfide mixture mixed with the product gas contacts a selective solvent system. The solvent used in unit 44 for selectively removing hydrogen sulfide from the gaseous stream is preferably an amine. The concentrated hydrogen sulfide stream is withdrawn from the bottom of unit 44 through line 45 for routing to further recovery processes. The product gas, substantially free of hydrogen sulfide, passes from the unit 44 through line 46 for introduction into carbon dioxide removal unit 48. The product gas is contacted with a suitable solvent fed to the unit 48 for removing carbon dioxide from the product gas. The rich solvent stream is extracted from the bottom of the unit 48 through line 50 for routing to subsequent recovery process. The purified product gas passes from the removal unit 48 to line 52. This accomplishes almost complete removal of hydrogen sulfide and up to 99% carbon dioxide removal. Furthermore, the product gas contains at this point more than 90% methane by volume. The washed product is passed through heat exchanger 38 from line 52 and passes through line 53 to heat exchanger 54 for additional heating before the methane rich gas if fed through line 56 to a guard chamber (not shown) containing pelleted zinc oxide for the removal of traces of sulfur compounds that remain in the gas and then to a final conventional fixed bed methanator 58. The guard catalyst can be of any fine materials on the market such as C7 or G72D sold by United Catalysts and the methanation catalyst can be one of the fine high nickel methanation catalysts sold under the name C150. The hydrogen in methanator 58 converts approximately 95% or more of the remaining carbon monoxide to methane and 50% of the remaining carbon dioxide to methane in the process gas to methane and yields a pipe line gas containing over 90% methane and less than 0.1% carbon monoxide by volume. The fuel gas from the methanator 58 is passed through heat exchanger 54 through line 60 and after further cooling and drying is ready for delivery to the pipe line. A word is appropriate here as to the steam to gas ratio (S/G) and as to the hydrogen to carbon monoxide ratio (H:CO) entering the methanator 30 via line 28. It is as previously mentioned, necessary to provide sufficient hydrogen so that the H:CO ratio equals and preferably exceeds 3:1. It will be appreciated, of course, that the stochiometric amount of hydrogen necessary to completely convert the carbon monoxide to methane is 3:1.

This can be accomplished through the use of the shift reaction in reactor 24 whereby a portion of the crude gas is reacted with steam according to the well known water gas shift to produce hydrogen and $CO_2$. This utilizes sulfur tolerant shift catalysts such as C25 or G93. Further, steam produced through the quenching of the gasification product from line 20 in waste heat boiler 21 can be utilized in the CO conversion reaction at minimal cost.

As previously indicated further, an object of this invention is to selectively hydrogenate carbon monoxide to methane while minimizing the reaction of carbon monoxide and steam to form more hydrogen and water. Therefore, the temperature in the inlet has been raised purposely since the higher temperature favors the methanation reaction and the lower temperature favors the shift reaction. This is only possible, however, through the use of a special catalyst since it would be normally expected that the higher temperature

$$CO + 2H_2 \rightleftarrows CH_4 + H_2O$$

would push the reaction to the left.

Both the reforming reaction and the shift reaction, however, are favored by a higher concentration of steam. Therefore, according to this invention the steam to gas ratio is maintained at less than 0.2 to 1. Normally there will be some steam in the process gases so that the steam to gas ratio would be at least 0.002. A steam to gas ratio of about 0.02:1 to 0.2:1 would reflect a more optimum range for the invention. We have found that as the steam to gas ratio exceeds 0.2 to 1, the shift reaction is favored.

The catalyst utilized in the reactor comprises the oxides of nickel mixed with the oxides of chromium. However, the unexpected improvement occurs when these materials are supported on or coprecipitated with magnesium aluminate or magnesium silicate. While the terms "aluminate" and "silicate" are utilized throughout the specification and claims, it is not absolutely clear that these compounds exist in these forms during use. It is possible that the silicon oxide or the aluminum oxide in some way influences the crystalline structure of the catalyst or that the nickel oxide and/or the magnesium oxide is somehow dispersed in a network of the chromium and aluminum oxides or sulfides. Further there has been some suggestion that the activity of the catalyst after sulfiding or after use in the process is due to a sulfide:sulfate relationship of the heavy metals. We do not wish to be bound by any theory or hypothesis as to the synergistic effect of the constituents of this catalyst. We do wish to state that the absence of any one of the components appears to deleteriously affect the synergistic effect of the quarternary system. Further, the catalysts were prepared by coprecipitation. This does not mean that other systems of preparation are not suitable. The formation of metal ammine carbonates with subsequent thermal decomposition is felt to be equivalent to coprecipitation from a solution of acid soluble salts. The phrase "intimate association of oxides or sulfides" thus contemplates these and other methods of preparation as being equivalent.

As will be brought out more clearly, addition of other constituents, such as vanadium oxide does not unduly effect the activity of the catalyst in a deleterious manner. It does not appear to have a particularly advantageous effect. It would appear, therefore, that the preferred catalyst of this invention, which will allow methanation, to the substantial exclusion of shift conversion, and will operate at low steam to gas ratios and at relatively high temperatures without carbon formation comprises the oxides and sulfides of nickel and chromium supported on the silicates and aluminates of magnesia. It will be appreciated that the recycled product gas from line 35 will act as a diluent, and will limit the amount of carbon monoxide entering the inlet 28 of the methanator. Further, the cooled gas will to some extent act as a heat sink. This gas, however, is not as effective as a heat sink as is steam. However, the steam is kept at a relative minimum so that the steam to gas ratio is less than 0.2:1.

It is possible of course to bring the gases into the methanation reactor at lower temperatures and the catalyst is effective at a temperature as low as 800° F. The lower temperatures do appear, however, to favor the shift reaction and higher inlet temperatures should be used if possible without an extreme rise in the exotherm. It is of course understood that the gases can be brought in at the higher temperature so long as the outlet temperature is not in excess of 1300° F. Temperatures in excess of that will tend to push the methanation reaction to the left.

TEST PROCEDURE

All of the catalysts tested were in the form of one-eighth inch by one-eighth inch tablets. The catalysts were loaded into the laboratory reactors and reduced for 16 hours at 700° and at a pressure of 50 to 100 PSIG by passing a mixture containing hydrogen and 0.6% $H_2S$ contained therein over the catalyst at a space velocity of 2000. Space velocity is defined as the volume of dry gas passed over a volume of catalyst per hour. The test conditions were as follows. Each of the reactors contained 10 ccs of catalyst; the pressure was at 500 PSIG; the catalyst was tested at inlet temperatures of 800, 1000 and 1100 degrees and at a space velocity of 10,000. The gas composition was adjusted to simulate that from the gasifier. This is shown according to the TABLE I as follows. The temperatures shown in the table reflect the inlet and outlet temperatures assuming methanation to equilibrium.

TABLE I

| RECYCLE/FEED | INLET SG | % CO | % $CO_2$ | % $H_2$ | % $CH_4$ | Temp. |
|---|---|---|---|---|---|---|
| Feed gas only | .0024 | 19.4 | 2.52 | 67.8 | 10.3 | |
| 2.7/1 | .4363 | 5.32 | 3.21 | 27.72 | 63.75 | 500–850 |
| 2.1:1 | .3582 | 6.50 | 3.97 | 34.40 | 55.13 | 500–950 |
| 1.6:1 | .2786 | 8.08 | 4.49 | 41.35 | 46.07 | 500–1050 |
| 1.2/1 | .2052 | 10.11 | 4.61 | 47.98 | 37.30 | 500–1150 |

Additionally, the gas contained 1 to 5 parts per million of $H_2S$. Gas compositions were selected as being typical of a Lurgi coal gasification process with a gas recycle at the methanator as previously indicated. Catalyst testing was performed with various recycle feed gas ratio compositions. The recycle/feed ratio limits the temperature rise by limiting the amount of CO available for hydrogenation. If catalytic efficiency is decreased (as for example by sulfur poisoning) so that equilibrium is not reached, the temperature rise will be lowered correspondingly. In that event the recycle rates would have to be adjusted from those shown in TABLE I. The S/G is the ratio of moles of steam to moles of dry gas.

PREPARATION OF THE CATALYST

Essentially all of the catalysts were made in the same way. The metal salts normally were in the form of nitrates and sodium carbonate was used as the precipitating agent. After the precipitate was made, it was filtered, washed, refiltered and rewashed and finally calcined. The calcined oxides were then ground to a fine mesh mixed with graphite and formed into one-eighth inch by one-eighth inch tablets. The catalyst tablets were then calcined to remove any remaining water. The method of preparation and testing will be better understood upon review of the following examples.

EXAMPLE 1

This catalyst consisted of nickel oxide and chromium oxide all supported on magnesium silicate. The catalyst was made from four separate solutions.

Solution 1 contained 55.5 parts per weight of magnesium oxide to which 180 volumes of nitric acid were added. 50 parts of deionized water was added thereto.

Solution 2 consists of 262 parts per weight of one normal sodium silicate and 490 volumes of deionized water.

Solution 3 consisted of 617 parts per weight of sodium carbonate dissolved in 3.850 volumes of deionized water.

Solution 4 consisted of 990 parts per weight of nickel nitrate and that is (Ni $NO_3.6H_2O$) 666 parts per weight of chromium nitrate (Cr $(NO_3)_3.9H_2O$) dissolved in 1,064 volumes of deionized water. Solution 1 was added to solution 2 with stirring. The combination of solutions 1 and 2 was then added to solution 3 with stirring at a temperature of 120° F. The pH at this point was 9.55. Solution 4 was added to the combinations of solutions 1, 2 and 3 with agitation and at a temperature of 140° F. The pH reached 7.0 before all the solutions has been added. In order to keep the pH above 7.0 an additional 190 parts of sodium carbonate in a 15% solution of deionized water was added. The final pH was 6.9. The slurry was heated to 160° F. and held to one-half hour with agitation. The pH climbed to 7.7 at this point. The slurry was filtered and washed with 5,000 volumes of deionized water. The material was then again filtered and rewashed. The washed filtrate was dried and calcined and tableted into one-eighth inch by one-eighth inch tablets. The finished tablets were recalcined. The finished catalyst contained:

NiO-49.7%; $Cr_2O_3$-25.3%; $MgSiO_3$-25.0%

The surface area of the new catalyst was 191 $m^2$/gram. After testing the surface area was reduced to 96.5 $m^2$/gram. The catalyst was tested according to the procedure previously mentioned. The run lasted for 75 hours and several values were taken. The attached table II indicates an average of the values recorded during the 75 hours run under various conditions.

EXAMPLE 2

This catalyst was formed by adding 990 grams of nickel nitrate to 660 grams of chromium nitrate and 1.070 grams of aluminum nitrate and 39 grams of magnesium oxide dissolved in 127 milliliters of nitric acid and 50 milliliters of water. This solution was diluted to 3,505 grams total with deionized water and heated to 140° F. A second solution containing 923 grams of sodium carbonate was dissolved in 5,280 milliliters of deionized water which was heated to 140° F. The metal nitrates were added to the sodium carbonate solution at the rate of 75 milliliters per minute and at a temperature of 140° F. Again the pH reached 7 before all of the metal solution had been added so that 20% more of sodium carbonate solution was added to the water to get all the metal solution into the precipitate. The final pH was 7.2. This solution was heated to 150° F. and agitated for one hour during which time the pH rose to 7.7. The material was filtered and washed and refiltered and rewashed. This procedure was continued for four filtrations and four washes. Thereafter the filtrate was dried and calcined. This material was then ground to a fine powder, tableted and recalcined. The final concentration of the catalyst was:

NiO-49.7%; $Cr_2O_3$-25.3%; $MgAl_2O_4$-25.0%

The surface area of the new catalyst was 208 $m^2$/gram. After 75 hours of testing, the surface area was reduced to 84.3 $m^2$/gram.

EXAMPLE 3

This catalyst contained:

NiO-75%; $MgSiO_3$-25%

The catalyst was prepared by mixing the nitrates of nickel and magnesium with the sodium salt of silica and precipitating same by the addition of sodium carbonate. The precipitate was filtered and washed following the steps generally indicated in the previous examples and finally after drying and calcining formed into catalyst pellets. The surface area of the finished catalyst was 190 m$^2$/gram. After 34 hours of testing the surface area was lowered to 104 m$^2$/gram.

EXAMPLE 4

This catalyst contained on a finished basis the following constituents:

NiO-75%; MgAl$_2$O$_4$-25%

Again, this catalyst was prepared as previously outlined by precipitation from an aqueous nitrate solution. The surface area of the finished catalyst was 135 m$^2$/gram which was reduced after testing for 34 hours to 46.1 m$^2$/gram.

EXAMPLE 5

This catalyst on a finished basis contained the following constituents:

NiO-50.5%; Cr$_2$O$_3$-49.5%

The catalyst was prepared by the procedure previously outlined involving the slow addition of sodium carbnate to a mixture of nickel nitrate and chromium nitrate. The surface area of the new catalyst was 65 m$^2$/gram which was reduced after testing for 58 hours to 5.7 m$^2$/gram.

EXAMPLE 6

This catalyst was prepared to have a nominal nickel to chromium ratio of NiO:Cr$_2$O$_3$ of about 2:1. The actual composition was as follows:

NiO-66.4%; Cr$_2$O$_3$-33.6%

The catalyst again was made by precipitation from a solution of metal nitrates by the addition of sodium carbonate. The surface area of the finished catalyst was 101 m$^2$/gram. The surface area of the used catalyst after testing for 88 hours was 13.2 m$^2$/gram.

EXAMPLE 7

This catalyst contained the following constituents on a finished basis:

NiO-55.9%; MnO-18.4%; Al$_2$O$_3$-25.7%

It was prepared by the addition of sodium carbonate to a solution of the metal nitrates. The surface area of the new catalyst was 209 m$^2$/gram. No surface area reading was determined for the used catalyst after a run of 68 hours.

EXAMPLE 8

This catalyst contained the following constituents:

Fe$_2$O$_3$-75.3%; V$_2$O$_5$-1.76%; Al$_2$O$_3$-24.6%

The catalyst was prepared as previously mentioned by precipitation from a solution of the metal nitrates. The new catalyst had a surface area of 132 m$^2$/gram which was reduced to 35.9 m$^2$/gram after a run of 68 hours.

EXAMPLE 9

The catalyst pellets of Example 5 were impregnated with chloroplatinic acid. The finished catalyst had a composition by weight of:

NiO-50.5%; Cr$_2$O$_3$-49.5%; Pt-0.1%

EXAMPLE 10

This catalyst contained the following constituents:

NiO-71.4%; Al$_2$O$_3$-28.6%

It again was prepared by the addition of sodium carbonate to a solution of aluminum and nickel nitrates followed by the steps previously outlined. The surface area of the new catalyst was 226 m$^2$/gram which was reduced to 58.5 m$^2$/gram after a run of 36 hours.

EXAMPLE 11

This catalyst contained the following constituents:

NiO-48.7%; Cr$_2$O$_3$-24.8%; V$_2$O$_5$-2.0%; MgSiO$_3$-24.5%

The catalyst was prepared by the same general procedures as previously indicated, i.e. precipitation of the metal constituents from a solution of their nitrates by the addition of sodium carbonate thereto. The finished catalyst had a surface area of 219 m$^2$/gram which was reduced to 134 m$^2$/gram after a run of 36 hours.

EXAMPLE 12

This catalyst contained the following constituents:

Pt-0.5%; MgSiO$_3$-99.5%

The magnesium silicate carrier was made by the method previously mentioned. After being formed and calcined for the second time the carrier was impregnated with a solution of chloroplatinic acid and again calcined to decompose the chloroplatinic acid to the oxide.

The finished catalyst had a surface area of 190 m$^2$/gram which was reduced after a 22 hour run to 152.8 m$^2$/gram.

EXAMPLE 13

This catalyst contained the following constituents:

Ru-0.5%; MgSiO$_3$-99.5%

The catalyst again was prepared in essentially the same manner as that of the platinum catalyst except that the magnesium silicate tablets were immersed into an acidic salt of ruthenium.

This catalyst had an initial surface are of 170 m$^2$/gram which was reduced after a 22 hour run to 83.9 m$^2$/gram.

EXAMPLE 14

This catalyst contained the following constituents:

NiO-73%; V$_2$O$_5$-2%; MgSiO$_3$-25%

This catalyst again was prepared according to the general procedure previously set forth. The surface area of the finished catalyst was 216 m$^2$/gram which was reduced to 28 m$^2$/gram after a run of 18 hours.

This series of catalysts and many other compositions were tested. These compositions were selected in order to represent the observations made during the procedure previously shown. As previously has been indicated the two major reactions that could occur under these circumstances are the classic water gas shift and the methanation reaction. The water gas shift is $$CO + H_2O \rightleftharpoons CO_2 + H_2$$

The methanation reaction is represented as follows:

$$CO + 3H_2 \rightleftharpoons CH_4 + H_2O$$

As previously indicated, according to Kirk-Othmer and other sources the methanation reaction proceeds from left to right at temperatures up to 1000° F. Above that temperature, these sources indicate that the reaction tends to go to the left.

The carbon monoxide shift reaction is also favored at temperatures below 1000° F.

Table II indicates the average methanation conversion, that is %CO to $CH_4$, and the amount of CO shift i.e. CO to $CO_2$ which occurred under various conditions and with various catalyst compositions. All of the test conditions were essentially the same. The inlet temperature was maintained at 800° F., however, where an asterisk occurs this indicates that the temperature was raised to 1100° F. Each of the data points represent many, many measured data points taken during the hours in which the catalyst was on stream. However, these data points do represent accurately the average percent carbon monoxide reaction at 800° F. and at 1100° F.

Referring now to Table II, the catalyst of Example 1, which is one of the catalysts of this invention, had an activity for the methanation reaction of only 2.6 at 800° when the steam to gas ratio was 0.443. The catalyst was active (53.7% CO to $CO_2$) for the undesirable shift reaction at that temperature and with that steam gas ratio. However, when the temperature was raised to 1100° and the steam to gas ratio lowered to 0.320 the shift reaction activity was reduced to 0.93 while the methanation reaction was increased to 61.7. Decreasing the steam to gas ratio even more to 0.061 increased the percentage of CO converted to $CH_4$ to 67.3 at 1100° F.

The nickel oxide-chromium oxide-magnesium aluminate catalyst of Example 2 likewise showed fairly poor results at a temperature of 800° with a high steam to gas ratio of 0.458. However, upon raising the temperature to 1100° F. and decreasing the steam to gas ratio to 0.199, the activity for the percent CO converted to $CH_4$ was raised to 53.7 and the percent CO converted to $CO_2$ via the shift reaction was reduced from 9.3 to 5.2. Still reducing the steam to gas ratio even more, to 0.095 this catalyst produced a negative shift, (pushed the shift reaction from right to left, i.e. from $CO_2$ to CO) with a concommitant maintenance of percent CO to $CH_4$ produced of 50.1%.

Since it is necessary to recycle the product gas, as previously indicated for purposes of controlling the temperature rise in the reactor, the lowering of the undesirable shift reaction is important. Since the gases are recycled, any unreacted carbon monoxide will ultimately be hydrogenated to methane. Carbon dioxide, on the other hand, is much more difficult to hydrogenate to methane and for the purpose of synthesis gas production, is essentially useless.

Having found that the nickel chrome composition coprecipitated with magnesium silicate showed good activity, a catalyst was prepared with the chromium deleted in Example 3. In this case, the catalyst contained nickel on magnesium silicate. This catalyst did not have very good activity for the shift reaction and had even poorer activity for the methanation reaction. Reducing the steam to gas ratio to 0.196 and raising the temperature to 1100° F. was not extremely helpful in increasing the activity for methanation.

In Example 4 the nickel catalyst was coprecipitated on a magnesium aluminate type carrier, and again the catalyst showed only moderate activity for the methanation reaction.

It was therefore determined that the two major catalytic constituents, i.e. nickel and chromium oxide should be tested without the support materials and these catalysts were only mediocre for the methanation reaction. The nickel to chromium oxide ratio was raised to 2 nickel to 1 chromium oxide without substantial increase or change in activity for the methanation reaction. The constituent nickel was then tried with manganese and aluminum oxide and again the catalyst showed relatively mediocre activity for the methanation reaction but did show relatively good activity for the shift reaction. The catalyst of Example 8 comprising the oxides of iron vanadium on aluminum oxide was tested with only mediocre results for the methanation reaction. Platinum was added in Example 9 to the catalyst of Example 5 without substantially increasing the activity for the desired reaction. The classic methanation catalyst, that is nickel on aluminum oxide, showed very poor activity under these conditions (with hydrogen sulfide present) for methanation of CO to $CH_4$. It will be remembered that this catalyst is extremely active for this reaction, but is extremely sensitive to poisoning by sulfur compounds. Furthermore, a temperature in the range of 1100° F. with a low S/G ratio has been considered extremely conducive to carbon deposition. However, with catalysts of this invention and under these conditions in which the gas contains small amounts of sulfur compounds no problem was encountered with carbon deposition with any of these catalysts.

Again vanadium was added in Example 11 to the catalyst of Example 1, and this catalyst showed fair activity for the methanation reaction at the low steam to gas ratio. This would indicate, therefore, that the vanadium did not appreciably hurt the activity, but did not increase the activity over the activity shown in Example 1.

In Example 12, a small amount of platinum was impregnated on the magnesium silicate carrier with extremely poor results for the methanation reaction.

The Example 13 ruthenium magnesium slicate catalyst was even less active than the platinum catalyst.

In Example 14 vanadium was added to the nickel magnesium silicate catalyst with essentially no increase in activity over the nickel on magnesium silicate of Example 3.

A catalyst containing the oxides of nickel chromium and magnesium was prepared and tested. This catalyst exhibited only moderate activity.

It is quite clear that the catalysts of this invention do selectively promote the reaction of carbon monoxide and hydrogen to produce methane at relatively high temperatures and at relatively low steam to gas ratios. Our previous experience had indicated that at these temperatures, with a sulfur free gas, that the catalyst would quickly plug up due to carbon deposition. This, however, was not experienced here. Furthermore, to prevent carbon it had previously been the practice to add large amounts of steam. Our experience here, on the other hand, indicated that the larger the steam to gas ratio the more the undesirable shift reaction was promoted. Further, we found that it was not necessary to use a large steam to gas ratio to prevent carbon formation and in fact the lower the steam to gas ratio the more selective was the catalyst toward the promotion of the desired reaction of CO to $CH_4$.

The catalyst of this invention, in the absence of sulfur in the process gas after reduction with pure hydrogen, had a low temperature methanation activity (500° F.) as good as that of conventional nickel methanation catalyst. The catalyst of this invention in the presence of sulfur, however, did not operate to produce acceptable conversions of methane at low temperatures of from 500° to 800° F. Further, all of the catalysts were first reduced with $H_2S$ and the sulfur concentrations of the catalysts were determined after reduction and after testing was made. It was found that chromium oxide in the catalyst serves both to provide a synergistic effect with the nickel, in the presence of magnesium aluminate or in the presence of magnesium slicate, and it helped further in inhibiting sulfur pickup.

Further, the loss of surface area appeared to be independent of the extent of sulfur pickup. Lowering the feed gas space velocity did not improve the catalytic activity.

This data showed a synergistic effect of catalytic constituents nickel oxide, chromium oxide and magnesium aluminate or silicate when coprecipitated. The data also tended to show that any of the constituents by themselves or three of the constituents without the fourth, did not provide this synergistic effect. Data further showed that the addition of still a fifth constituent, i.e such as vanadium, had little effect one way or the other as to the activity or the selectivity of the catalyst for the desired reaction. What was surprising, however, was that the catalyst was active at higher temperatures, i.e. those which would tend to approach the reforming reaction, in which the methanation reaction would be pushed to the left. But this did not occur. Furthermore, while some of the temperatures were in the carbon forming range, with extremely low steam to gas ratio, there was no problem with carbon deposition even with extremely low steam to gas ratios.

The data indicated that the lower the steam to gas ratio the more selective was the catalyst toward CO conversion to methane. Accordingly, the catalysts of Examples 1 and 2 were tested in two separate long term runs, in which the steam to gas ratio was varied.

The results of these tests are shown in Table III.

Please note that the nickel chromium oxide catalyst on magnesium silicate in runs 19 showed an increase in CO conversion to methane from 44.9% to 69.4% with a reduction in steam to gas ratio of 2.47 down to 0.034. Simultaneously, at the lower steam to gas ratios the shift reaction was shifted to the left. In other words, some of the carbon dioxide in the initial gas stream was being converted to carbon monoxide which then could be converted to methane by reaction with hydrogen. Please note that at the steam to gas ratio of 0.075 the CO shift reaction showed a minus 6.3 and at 0.034 showed a minus 5.6 shift reaction. This minus would indicate a shift to the left.

The nickel chromium oxide catalyst on magnesium aluminate again showed good activity for carbon monoxide to methane. The activity was not quite as good as the Catalyst 1, but at the lower steam to gas ratio was well above 40%.

Again run 27 added some lower temperatures and a broader range of steam to gas ratios. It will be seen that the catalyst of Example 1 at the high steam to gas ratios, i.e. above 0.3, had a relatively low activity for the methanation reaction and a relatively high activity for the shift reaction. However, as the temperature was raised to 1100° and the steam to gas ratio reduced down to 0.045–0.075, the methanation reaction activity was raised in one case to 83.9 and a minus CO shift to 12.6.

Essentially the same activities were noted with nickel and chromium oxide on magnesium aluminate. At the higher steam to gas ratio of 0.352 and at 700° F. the shift reaction predominated with a 68.7% conversion with only a 7.4 in one instance and a 23.3% methanation reaction in another. At the low steam to gas ratio the carbon monoxide shift reaction was pushed to the left to produce more CO which was in turn hydrogenated to produce more methane.

This data illustrated that as the steam:gas ratio exceeds 0.2:1 that there is a trend toward more $CO_2$ production. This is especially true at lower temperatures.

It appears then that the invention includes not only the specific catalyst utilized but the observation that with these catalysts the reactions can be quite selective for the conversion of CO to $CH_4$ by hydrogenation rather than the conversion of CO to $CO_2$ through the water gas shift at higher temperatures or a lower steam to gas ratios. The surprising absence of the problem of carbon deposition with low steam to gas ratios at the higher temperatures also is part of this invention.

Many modifications will occur to those skilled in the art from the detailed description hereinabove given and such is meant to be illustrative in nature and non-limiting except so as to be commensurate in the scope with the appended claims.

We claim:

1. A sulfactive and selective methanation catalyst, having the property of inhibiting the deposition of carbon under normal carbonforming conditions at low steam/gas ratios of less than 0.320:1, the property of selectively promoting the conversion of carbon oxides to methane to the substantial exclusion of converting carbon monoxide to carbon dioxide at low steam/gas ratios, and the property of actively and selectively converting carbon oxides to methane in the presence of sulfur compounds at temperatures in excess of 1000° F. but less than 1250° F., which comprises:
   A. the oxides and sulfides of nickel and chromium in intimate combination with a compound selected from the group consisting of the aluminates or silicates of magnesia;
      1. the nickel and chromium components, expressed as the oxides, comprising a major proportion of the total weight of the finished catalyst;
      2. the aluminates or silicates of magnesia comprising a minor proportion of the total weight of the finished catalyst;
   B. said catalyst having a surface area, before being placed onstream, in excess of 100 m²/gm; and in which
   C. the steps of catalyst preparation having included coprecipitation of insoluble compounds of nickel, chromium, magnesium, and aluminum or silicon from aqueous solutions of soluble salts of said metals.

2. A methanation catalyst, as defined in claim 1, in which the coprecipitation involves the following:

A. forming an aqueous solution of nickel, chromium, magnesium and aluminum salts; and
B. adding an alkaline solution to said aqueous solution of metal salts; and
C. precipitating insoluble metal salts from said aqueous solution.

3. A methanation catalyst, as defined in claim 1, in which the coprecipitation comprises the steps of:
   A. forming an aqueous solution of salts of nickel, chromium, and magnesium;
   B. forming an aqueous solution of a salt of silicon;
   C. mixing the two aqueous solutions together;
   D. slowly adding a precipitating agent to said mixture of said salt solutions; and
   E. precipitating insoluble metal salts from said aqueous solutions.

4. A sulfactive methanation catalyst, as defined in claim 1, in which the coprecipitation comprises the steps of:
   A. forming an aqueous solution of the salts of nickel, chrmium, magnesium, and aluminum;
   B. slowly adding said solution to an aqueous solution of an alkaline precipitating agent and bringing the pH of the solution up to about 7;
   C. precipitating insoluble metal salts from said aqueous solution;
   D. filtering the material and forming a filter cake;
   E. washing said filter cake and refiltering same;
   F. drying and filter cake and calcining at a temperature of at least 700° F.;
   G. grinding said filter cake to a fine mesh powder;
   H. mixing said fine mesh powder with a lubricant; and
   I. forming said fine mesh powder into shaped catalyst.

5. A sulfactive catalyst, as defined in claim 1, in which said coprecipitation comprises:
   A. forming an aqueous solution consisting of adding magnesium oxide to nitric acid;
   B. forming an aqueous solution consisting of sodium silicate and deionized water;
   C. forming a solution of nickel and chromium salts by dissolving same in acid and deionized water;
   D. forming an aqueous basic solution as a precipitating agent;
   E. mixing the solutions A and B together with stirring, and thereafter adding solutions A and B to solution D;
   F. adding solution C to the solutions of A, B, and D, and adjusting the pH of the mixture to about 7 to form a slurry;
   G. filtering the slurry to form a filter cake;
   H. washing said filter cake with deionized water;
   I. drying and calcining the filter cake at a temperature of at least 700° F.;
   J. grinding the calcined material into a fine mesh powder and mixing said powder with a lubricant; and
   K. forming the mixture of the fine mesh powder and lubricant into formed catalyst tablets.

6. A catalyst, as defined in claim 1, in which the nickel compound of the finished catalyst, expressed as the oxide, comprises about one-half of the weight of the finished catalyst.

7. A catalyst, as defined in claim 1, in which the chromium component of the finished catalyst, expressed as $Cr_2O_3$, amounts to about one-fourth of the weight of the catalyst.

8. A catalyst, as defined in claim 1, in which the magnesium silicate or the magnesium aluminate amounts to about one-fourth of the weight of the finished catalyst.

* * * * *